United States Patent [19]

Cosman et al.

[11] Patent Number: 4,838,265
[45] Date of Patent: Jun. 13, 1989

[54] LOCALIZATION DEVICE FOR PROBE PLACEMENT UNDER CT SCANNER IMAGING

[76] Inventors: Eric R. Cosman, 872 Concord Ave., Belmont, Mass. 02178; Gary M. Onik, 9 Nancy Rd., Milton, Mass. 02186

[21] Appl. No.: 147,115

[22] Filed: Jan. 21, 1988

Related U.S. Application Data

[63] Continuation of Ser. No. 738,167, May 24, 1985, abandoned.

[51] Int. Cl.[4] .............................................. A61B 17/00
[52] U.S. Cl. ................................. 128/303 B; 128/630; 378/20; 378/164; 378/205
[58] Field of Search ...................... 128/303 B, 630, 653, 128/660, 774; 378/20, 163, 164, 205

[56] References Cited

U.S. PATENT DOCUMENTS

| | | | |
|---|---|---|---|
| 3,547,121 | 12/1970 | Cherry | 378/164 X |
| 3,812,842 | 5/1974 | Rodriguez | 378/163 X |
| 4,319,136 | 3/1982 | Jinkins | 378/163 X |
| 4,583,538 | 4/1986 | Onik et al. | 378/20 X |

Primary Examiner—Stephen F. Husar
Attorney, Agent, or Firm—Richard J. Birch

[57] ABSTRACT

A method and apparatus are presented here which allow for easy quantitative determination of a position on a patient's skin as seen in CT scanner images. It is based on a device which is a lattice of fiducial rods that can be placed on or near the patient's skin. The images from this device then enable specific points on the skin itself to be readily identified by the operator. It requires a minimum of complication or calculation, and can be used in a variety of procedures which involve placing a probe through the patient's skin to a target, such as a tumor, as seen on the CT scan. The localizaing ladder, as it will be called, can be quickly placed in an aligned fashion on the patient's body, and, depending on several embodiments of the invention, coordinate points on the skin can be determined thereafter by either CT scanner software output, a simple off-line numerical calculation, or, even simpler, counting of the ladder localizer points.

18 Claims, 4 Drawing Sheets

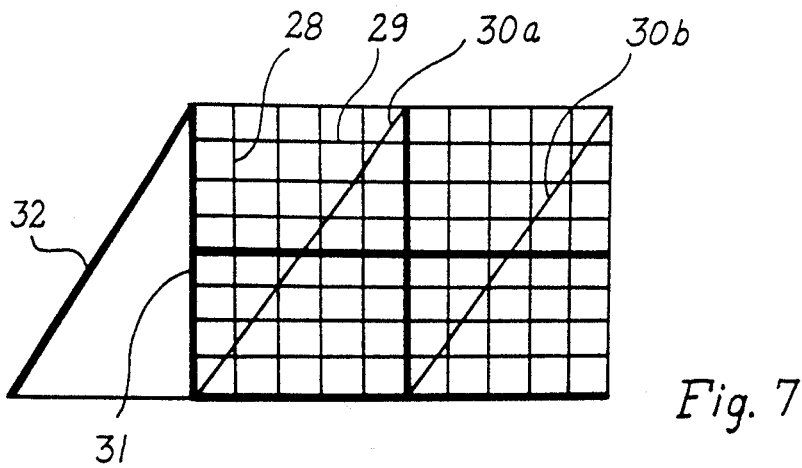
Fig. 7
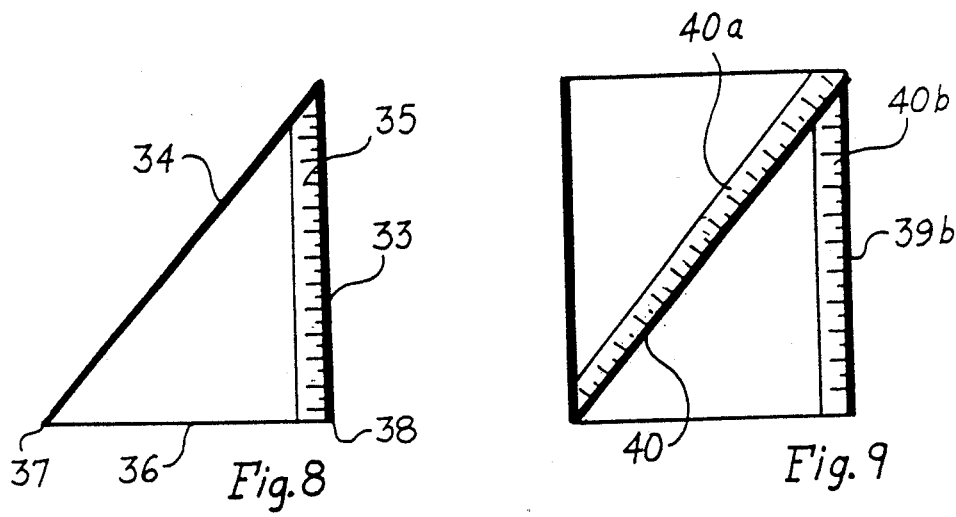
Fig. 8
Fig. 9
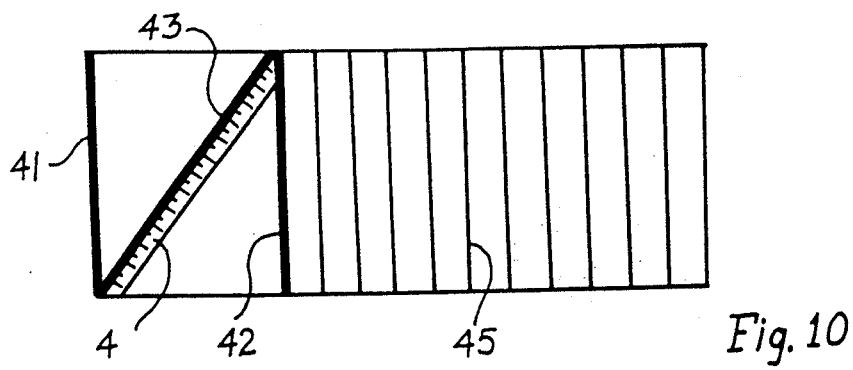
Fig. 10

LOCALIZATION DEVICE FOR PROBE PLACEMENT UNDER CT SCANNER IMAGING

This is a continuation of co-pending application Ser. No. 738,167, now abandoned, filed on May 24, 1985.

BACKGROUND OF THE INVENTION

It is a common practice in interventive radiology to identify a target as seen on computerized tomographic (CT) images and then seek that target through the skin by means of a probe. This probe might be a biopsy needle, drainage catheter, radionuclide catheter, radio frequency or microwave electrode, drug delivery catheter, etc. At the present time, the radiologists use essentially a free hand method, estimating the depth of the target from a point on the skin and also the angulation of the probe from that point to the target. For years a similar problem has been approached for the case of the brain. Here the situation is much simipler in that the skull represents a rigid anchoring platform onto which head rings and localizer systems can be permanently affixed. In this way exact referencing and stereotaxic direction of probes can be achieved in the brain. The body is a different matter. It has no rigid anchoring points and is prone to moving with respiration and patient movement. Respiratory gating and patient immobilization help, but still the problem is far more difficult than the head.

A simple means is needed for the radiologist to identify specific surface points on the skin that can be correlated with corresponding points on the CT image. The means of doing this must be straight forward and unambiguous. It also must circumvent the problem of body motion with respiration and patient movement. The means must be simple to apply and easy to understand and preferably give quantitative coordinates to the operator with a minumum of analysis.

The invention described herein is such a means. For the first time it provides a way to find reference points near or on the surface of the body of the patient over a wide area and over the curved surface of the body itself. By means of its lattice construction, which we will sometimes refer to as a ladder localizer, curvilinear coordinates over the body's surface can be identified discretely and orthogonal components may also be determined to provide a unique position on the patient's skin. Hereafter, we will refer to the principle axes of the scanner, which approximate the axes of the patient's body, as the z axis or the axial direction perpendicular to the scan slice, and the x and axes which together represent a Cartesian coordinate system as shown in FIG. 1. Thus we refer to an axial slice as one which is parallel to the x, y plane, a sagittal slice as one being parallel to the y, z plane, and a coronal slice as one being parallel to the x, z plane. These are essentially CT machine coordinate planes.

There has been very little prior art in such localizer systems, and none with the objectives that we have in mind. R. Brown, et al. (Investigative Radiology, Volume 14, Page 300, July, 1979); indicates a localizer system for use in brain stereotaxy. It is a rigid structure which can be attached rigidly to the skull by means of an intermediate head ring. It has N-type structures on its localizer which enables a point on the diagonal only to be determined. You cannot get a rod coordinate unless the localizer is aligned with the scanner beforehand. Brown's localizer is not designed to be placed near the skin for localizing a point on or near the skin. It is designed for localization of a plane which thereafter can be used to determine targets within the body. It teaches no use of scales affixed to the localizer for means of digitally finding a physical point on a rod or a diagonal. Brown's localizer is not adapted for placement close to or on the skin for the purposes described in our invention. It is also not used as part of a localizer where added rods beyond the two rods off the N-structure are used in order to determine the CT plane intersection of the added rods as further points near the skin.

Hammerschlag et al. Computed Tomography of the Spinal Canal, Radiology, Volume 121, Page 361, 1976 describe a skin marking system composed of polyethylene angiographic catheters, each of which differ in length. This system of catheters is designed to help determine the level or z axis (axial position) of the CT plane. The degree to which you can define the plane is no better than the quantum length differences between adjacent catheters, in their case being 1 cm. Thus, it is a discrete means, not a continuous means as in our invention, of z identification of the CT plane. The diagonal element in our invention provides a continuous means for plane identification and a means of determination of the plane intersection with both the diagonal and rod elements. Furthermore, the Hammerschlag system enables visualization of their catheters only on one side of the last catheter which is intersected, not on the entire array. This is again different from our invention and a limitation, whereas our rod elements are described as of equal length, all of which appear in the same scan. Hammerschlag describes no scale means on their set of catheters for quantitative z identification nor do they describe a diagonal element to give continuous plane and point localization determination. Thus, the Hammerschlag approach teaches only a crude means of achieving a level or z position of the plane which is unsuitable for the precise localization of a skin point for entry in a surgical procedure as we describe here.

BRIEF DESCRIPTION OF THE FIGURES

FIG. 7 shows a lattice type localizer for level and skin point determination in two nearly orthogonal directions.

FIG. 8 shows a simple triangular localizer system with a single rod and a single diagonal plus a scale.

FIG. 9 shows a very rudimentary skin localizer consisting of a single N-type structure with adjoining scales.

FIG. 10 shows a ladder localizer with an N-type structure at one end with a scale on the diaonal.

DESCRIPTION OF THE METHOD AND APPARATUS

Figure 1:
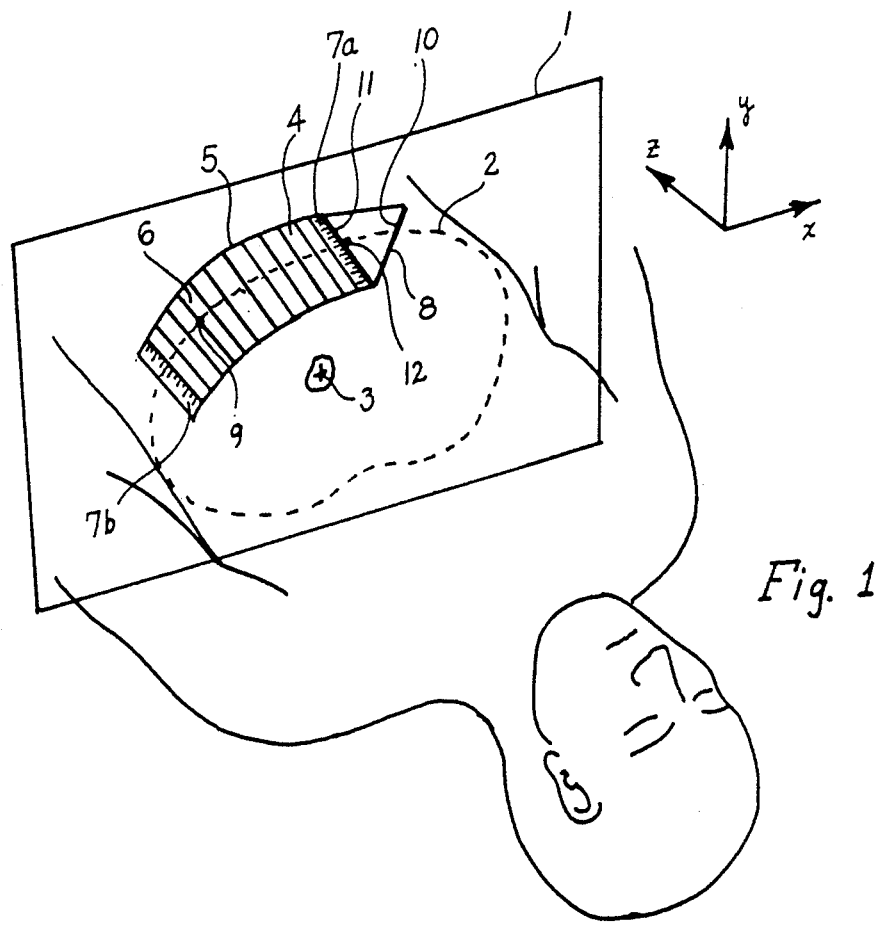
FIG. 1 shows a localizing ladder device placed on the patient's torso and aligned with the axial plane.
Figure 2:
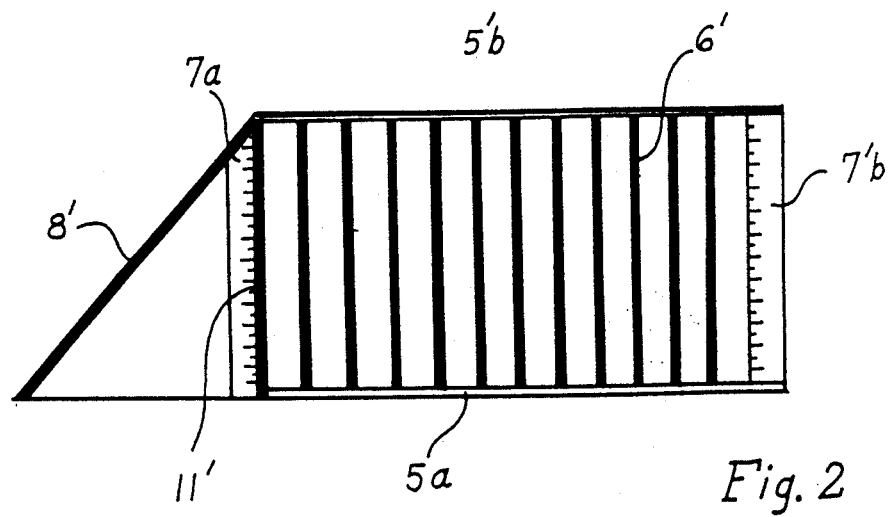
FIG. 2 shows a possible localizing ladder system with axial rods and a triangle attached on one end for z determination.

Here we describe a method and device which is used to identify a point on a patient's skin which has been visualized on a CT image. From that point on the skin, one can then pass a problem into the body to a target which is to be reached. This is illustrated schematically in FIG. 1. An axial CT plane 1 is shown in intersecting the body on a perimeter 2 with a target inside the body 3. The localizer system 4 is shown strapped to the patient's body with its lower edge 5, in this case, aligned parallel to the plan of the CT scan, or the axial plane. This alignment can easily be done by laser or other lights which are available on most CT scanners, that are aligned with edge 5 prior to placing the localizer on the surface. The localizer can be stuck down to the body by double sticky-back tape. One embodiment of the ladder localizer is shown in FIG. 2. Its lower edge $5'a$ corresponds to 5 in FIG. 1. It has rod-like ladder elements 6 in FIG. 1 and $6'$ in FIG. 2 which all run roughly parallel, although not necessarily parallel, and when stuck on as shown in FIG. 1 to the body, element 6 would be roughly parallel to the axial direction. The number of rod elements 6 can vary in number and interspace can also vary. The rod elements are attached between lower edge $5'a$ and upper edge $5'b$ in FIG. 2. On the ends are two scales, $7a$ and $7b$ and $7'a$ and $7'b$ shown in FIGS. 1 and 2, respectively. In addition, on one end there is a diagonal element 8 in FIG. 1 or $8'$ in FIG. 2. Thus, when scan section 2 is visualized, one will see a series of points representing the intersections 9 of the scan plane with rod 6 appearing as a series of dots on the image. At the triangle end the diagonal 8 will intersect the CT plane at point 10. And the first rod 11 of the ladder will be intersected at point 12 by the CT plane. If the angle between the diagonal and the parallel rod at the end is known, then by measuring the distance on the image between points 12 and 10, one can determine the position on scale $7a$ corresponding to the CT plane. If in addition the localizer is aligned to the CT plane beforehand, that same distance will be measured on scale $7b$ on the other end of the ladder. Thus, the operator can merely count the number of rods from, let us say, the triangle end to a point on the skin which he wishes to identify as the entrance point. He can then go to the physical localizer, count that number of rods, and the physical point of entry will then correspond to the intersection of that rod and the z position as measured on scale $7a$ and $7b$. This simple method then, in combination with the localizing ladder, enables the operator to determine a specific point desired on the skin. We can let that point, for illustration, be indicated by point 9 in FIG. 1. Then, if you wish to pass a probe through that point in space 9 to a target point 3 which is seen in the CT image, you could calculate the appropriate angles and depth penetration to do so.

Thus, the localizing ladder shown in FIG. 2 represents a way of setting up a coordinate system in space that maps image from the CT scan to the physical localizer itself. The localizer can be fixed to the patient by tape or other means. The rod 6 can be sufficiently narrow so that as not to obstruct passage of a probe. Elements 5, $5'a$, and $5'b$ can be flexible such as made of rubber so that the localizer can easily conform to the surface of the body. The same is true for the rod element 6. Rod element 6 must be made of such a material that they are radiopaque and thus visualizable on the CT image. If NMR applications rather than x-ray is desired, or if P.E.T. scanning (proton emission tomography) is used, the appropriate materials or sources for rod element 6 could be devised. Element 6 could also be flexible so that they could deform and hug the patient's body along the axial contour. The localizer could be placed on in other orientations if sagittal or coronal views were desired. If the ladder localizer is aligned to the axial plane as cited above, then the intersections of the rods to the CT plane represent specific fiducial points in a curvilinear coordinate system represented by the ladder. All that is required is the z position, which is determined by the triangle structure as described above, to determine the unique location of each intersection with the rods 6. Many materials could be chosen for element 6. Aluminum possibility as well as various impregnated silicones to achieve sufficient atomic density to show up well on CT scans. The same is true for the triangle elements $8'$ and $11'$ in FIG. 2. They might be made a different diameter or shape so as to distinguish them from the other rods $6'$. The ladder localizer could be made in a variety of lengths and can be supplied sterile and disposable. Double sticky-back tape on its underside enables easy attachment to the patient. It is noted that although the rod $6'$ may not precisely contact the skin, they still represent a fixed point in space; fixed in relationship to the patient's body independent of the body's macroscopic movement. This is an important feature of the embodiment shown in FIG. 2 as it circumvents the problems of body immobilization and the inaccuracies associated with respiration.

Figure 3:
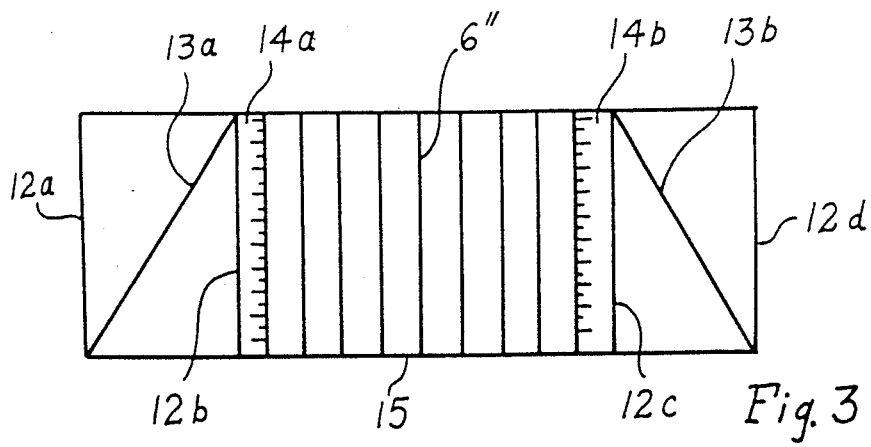
FIG. 3 shows another embodiment like FIG. 2 except that one each end there is an N or picket-fence structure to enable z coordination.

Another embodiment of the ladder localizer is shown in FIG. 3. In this case there are picket fence or "N-type" structures represented by rods $12a$, $12b$, $12c$, and $12d$, and diagonal elements $13a$ and $13b$. The intersection of the CT plane with an N-type structure gives a series of two rod images and one diagonal image, the latter being slightly elliptical shaped if the device is aligned with the scan as above. by calculating the proportional distances between the intersections of say $12a$, $13a$, and $12b$, one can calculate the exact intersection point with diagonal $13a$. This then fixes a specific point in space. A similar operation can be done for the N structure at the other end, giving it interesection point to diagonal $13b$. The line between these points thus lies in the CT plane. Its intersection with any of the rod elements $6''$ then fixes the physical point of the intersection of that rod as seen on the CT image. In this way, specific points referenced to the ladder localizer can be identified. The scales on each end $14a$ and $14b$ can serve to fix the z coordinate if the edge of the localizer 15 is aligned to the CT scan beforehand. This embodiment of the ladder localizer may involve only one N structure at one end or two of them on each end, as shown in FIG. 3.

Figure 4:
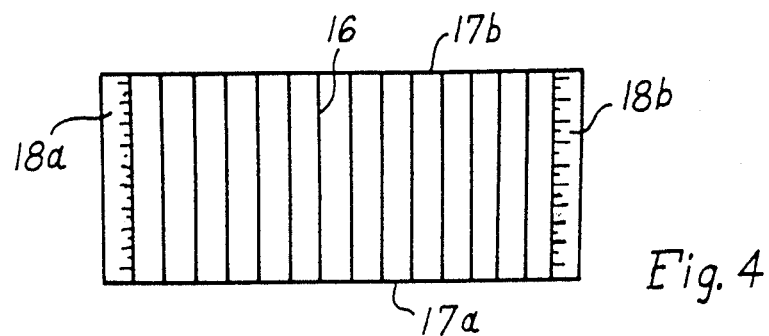
FIG. 4 shows a rudimentary ladder system without any diagonal elements which can be used in certain situations.

An even simpler ladder localizer still is shown in FIG. 4. In this case, only the rod elements 16 are in place attached to the transverse elements $17a$ and $17b$. Here only the intersections of the rod element 16 will shown up on the CT scan as there is no N structure or triangle at either end. In this case the device would be aligned with its edge 17a parallel to the scan lane. By use of precisely known table movements in the z direction, the exact position of the scan plane relative to the scales 18a and 18b might be known before hand. Thus, the z position on the localizer is predetermined in a sense. In that case the intersection with any of the rod elemnets 16 would again be mapped to a physical point at the localizer and thus relative to the patient's body.

Figure 5:
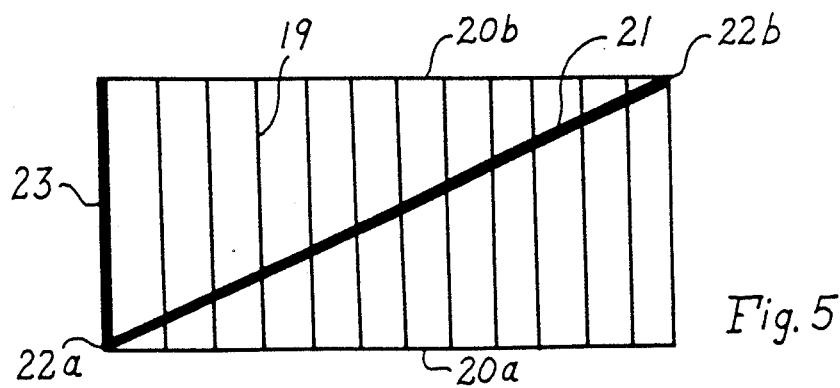
FIG. 5 shows a ladder localizer system with a diagonal element that overlaps the axial rods to provide a self-contained, two-dimensional curvilinear coordinate representation.

It is evident from the above discussion that the localizer ladders may be used without alignment of the upper or lower with the axial or CT plane, although such alignment makes use of the localizer simpler. Another embodiment of the ladder localizer which is shown in FIG. 5, eliminates further the need for either the triangle or N structure or table z position as discussed above. This localizer, as do the previous designs, has the rod elements 19 attached to the upper and lower elements 20a and 20b. In addition, there is now a diagonal element 21 which can be laid on top of the rod elements 19 and which spans in this illustration from one lower corner 22a to the upper corner 22b. Furthermore, the rod element on the end 23 could be of larger diameter than the other rods 19 so as to distinguish one end from the other in the CT image. For this device if the edges 20a and 20b were aligned approximately in the axial plane, the rod elements as usual would show up as a sequence of dots on the image, and the diagonal element 21 would appear as another image adjacent to this sequence of rod images. The central position of the intersection of the diagonal 21 as seen on the CT image could then be specified relative to the rod images. Thus, for example, by counting from the image of rod 23 the number of rod images to the image of diagonal 21, one can determine on the physical ladder localizer itself the exact position in space of the diagonal image intersection of 21. If the image of 21 is intermediate between two rods, one can interpolate visually where the central position of the intersection of the diagonal actually is on the physical localizer. By this means an absolute curvilinear coordinate system can be set up in space, and not only the locations of the ladder rod intersections but also the intersection of the diagonal provides the unique point on the localizer corresponding to the respective intersections. This kind of ladder localizer completely eliminates any quantitative calculation of the z coordinate altogether. By a process of simply counting rod images from one end to the intersection of the diagonal point, one determines the z coordinate. It is also notable that alignment of the upper and lower edges 20a and 20b with the CT plane is not necessary at all. This is due to the uniqueness of the overlap of the intersection of the diagonal and the rod images even if the CT plane is coming in at an oblique or non-parallel axis. Thus, this embodiment manifestly eliminates the need for alignment as well. The diagonal rod element 21 need not ride above or below the rods but could be molded integrally with them so that it is approximately in the same plane. The localizer thus becomes a web-like network from which a specific point of a plane intersecting it, though the network be curved on a arbitrary surface, can be determined. No quantitative relationship between rod distances or diagonal angle need by specified.

Figure 6:
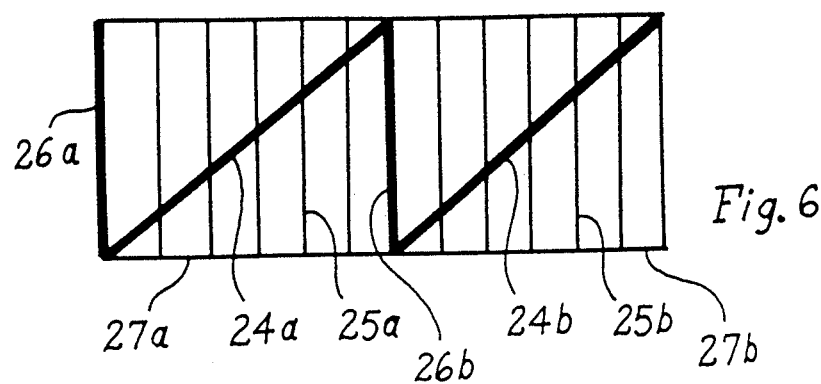
FIG. 6 shows a similar design to FIG. 5 except the ladder is broken into two components each with overlapping diagonal for higher resolution determination in the z direction.

If the obliqueness of the diagonal as illustrated in FIG. 5 is too shallow so that the determination of the intersection with it becomes unacceptably accurate, then another similar embodiment, as shown in FIG. 6, could be devised. In FIG. 6 the ladder localizer is divided into two sections; the first with diagonal element 24a and the second with diagonal element 24b. Rod elements 25a and 25b for each of the sections are of normal size, but rod elements 26a and 26b might be a larger size so that one can then distinguish between sections a and b. Thus, one has a ladder localizer which is a multiplicity of rod elelements as in the above examples but also having multiple diagonal rod structures so as to distinguish which section one is in. Because the diagonal 24a and 24b span fewer of the normal rod elements 25a and 25b, then the angle of the diagonal elements 24a and 24b with the lower edges 27a and 27b is steeper. In this way the elliptical interseciton of approximately an axial slice will be much smaller and the intersectional position with the diagonal much more accurately determined. Obviously localizer with larger numbers of sections can be devised.

Many variations of the above embodiments are possible. The rod elements can be of a variable size and shape ranging from linear elements with small, round cross section or square cross section to rectangular-shaped elements like flat straps. We may think of the rods as being elongated structures with a long axis which is roughly defined as the center of its section and run in the direction of its elongation. A variety of materials could be used for them to give them either a rigid consistency or malleability, or even total supple flexibility. Variations in the rod element size might also be possible to help index which rod you are looking at. For example, the end rod on one end could be large to indicate the direction of orientation of rods you are counting. The rods could have different lengths too, to distinguish which level or axial section one is in. If the rods are approximately in centimeter spacing, for example, every fifth rod could be larger diameter to help you count across them. It is not necessary that the rods be parallel or even straight. Since the CT image cuts across in one plane, and you are only counting rods, a specific point in space can be determined without parallelity. The transverse elements which hold the rod lattice or matrix together need not be perpendicular to the rod elements at all, nor do there have to be two elements as illustrated in FIG. 4, element 17a and 17b. In fact, there could be a multiplicity of such transverse elements such that the latter takes on the appearance of a mesh or a screen. In this way tomographic scans in planes perpendicular to the axial plane will intersect the transverse elements so as to have them assume the role of the rods in the discussion we have been giving in the above.

It is possible to extend the concepts described above to a lattice of rod elements which is possible to use for either axial, sagittal, or coronal tomographic images to localize a point on the skin. This is embodied in FIG. 7. The longitudinal rod elements 28 might be aligned approximately to the axial direction on the patient's skin. The transverse elements 29 would be approximately orthogonal to the longitudinal ements 28. There are diagonal elements 30a and 30b which act in the same way as the elements in FIG. 6, number 24a and 24b. There may or may not be an outboard or inboard traingle structure, illustrated in FIG. 7 by the end longitudinal element 31 and diagonal 32 from which quantitative distance measurements and thus longitudinal dimensions can be calculated as described above. Now an aixal slice may cut across, for illustration, the entire set of longitudinal rods 28, thus giving a set of images. In addition, one would be able to see the diagonal images 30a and 30b as discussed in connection with FIGS. 5 and 6. On the other hand, a tomographic slice in a direction perpendicular to the axial direction would cut across all of the transverse elements 29 and the diagonals either 30a or 30b as well. This would also give a series of image points analogous to those for the axial slice. In this way, positions from any orientation scan can be localized on the skin. Obviously, a triangle structure could be laid either on the top or the bottom or on the right-hand side in the FIG. 7 to implement dimensional calculations. It is not necessary that the longitudinal and transverse elements be exactly perpendicular or exactly aligned to the body axis or machine axial or transverse directions for spacial localization to be implemented. One might refer to this kind of device as a localizing lattice giving a full mapping of points for any tomographic scan.

For completeness, we show in FIG. 8 an even more rudimentary embodiment of the present invention which consists of a single rod and a single diagonal in a triangular connection. The rod element is 33 and the diagonal 34 connected in a fixed angular relationship with a scale 35 shown along and parallel to the rod 33. Edge 36 may indicate a sub-straight on which the rod and diagonal are connected, but may not be present and only be the imaginary line between the tip 37 of the diagonal 34 and the end 38 of the rod 33. This localizer could be placed on the skin with points 37 and 38 aligned with the axial plane by the CT machine laser lights and thus the intersection of a plane with 34 and 33 would give image points the distance between which could determine the location of the intersection along 33 as indicated by the scale 35.

FIG. 9 shows a simple N-structure with scales on it for skin localization. Rods 39a and 39b and diagonal 40 make up the N, which is rigid and planar and can be laid on the skin. Any CT plane cutting 39a, 39b, and 40b will produce three images from which the intersection point on 40 can be calculated by proportional division as per R. Brown, et al. This is not dependent on CT axial plane alignment as it is for the device of FIG. 8. Once the distance on 40 of the CT intersection of 40 is calculated, it may be read off of scale 40a directly thus simplifying the location of the intersection point, which lies near the skin. Once that point is known, by using translations along the CT machine x-y-z axes (as in FIG. 1), and assuming an axial CT scan plane or a CT plane of known angular tilt from the machine axial plane, the points of the CT plane intersection with rods 39a and 39b may be determined. In case the device is aligned as for that of FIG. 8, the rod scale 39b may be of similar use as for FIG. 8.

Figure 11:
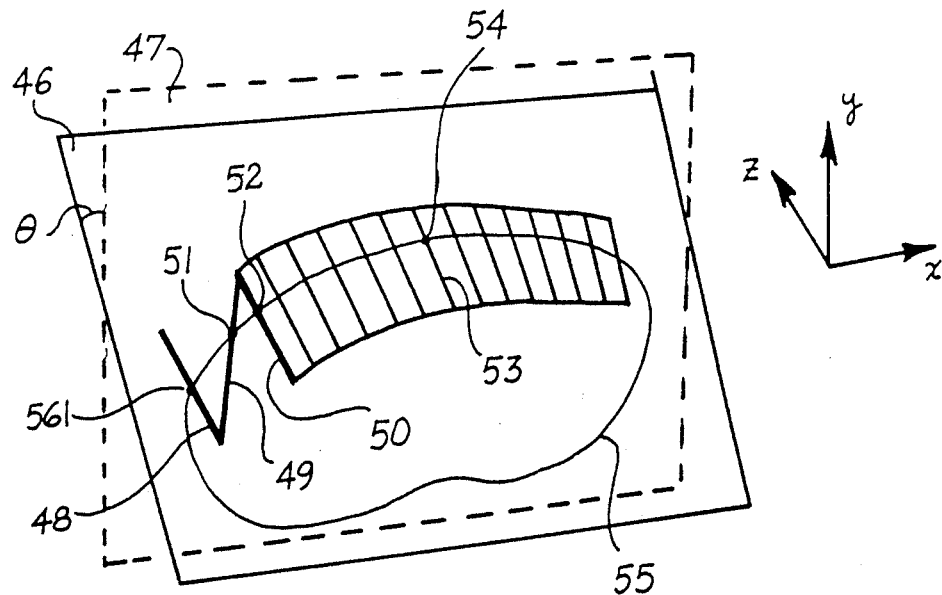
FIG. 11 shows how the device of FIG. 10 may be used for tilted CT p[lane approaches.

FIG. 10 illustrates another ladder localizer with an N-type end structure consisting of first rod 41, second rod 42, diagonal 43 non-parallel to 41 and 42, scale 44 aside 43, and a multiplicity of added rods illustrated by 45. This requires no pre-alignment in the CT scanner and is usable with oblique or tilted CT scan planes relative to the principle machine x-y-z axes. Its use is illustrated in FIG. 11 which shows an oblique plane 46 tilted at one angle $\theta$ to the CT machine axial plane 47 (which is the x-y plane). Now 47 cuts rod 48 at point 561, diagonal 49 at 51, and rod 50 at 52, and added rod 53 at 54. By seeing the images of 561, 51, and 52 on the CT image, and by taking ratios of distances between these images of rod 48, 52 and diagonal 51, one can determine the acutal physical points 51 on 49 as was shown by Brown, et al. By knowing $\theta$ and determining the relative coordinates of the images of 51 and 54 on the CT image, one can deduce the actual coordinate differences between actual point 51 and 54 in the x, y, z coordinate system of the CT scanner. Perimeter 55 may here represent the intersection of the CT plane with the patient's skin. Thus the device of FIG. 10 is useful for oblique CT cuts (not parallel to the CT axial plane) with a known angle of obliquity and where the localizer is not necessarily aligned in any way to the CT axial plane. That is, the CT scan plane may not be parallel to the x-y plane as shown in FIG. 1, but may be at some knonw oblique (tilt) angle to it; this angle can be read out in modern scanners. Usually the tilt anble is a rotation about the x-axis relative to the fixed machine axes. Nonetheless, the unique intersection point of diagonal 41 is determinable. Note that after calculating the intersection 51 of 49 in FIG. 11, one could measure off on 49 with a ruler to find 51. Alternatively, if there is a scale as part of the device near the diagonal, as is 44 near 43 in FIG. 10, one can simply read the scale to deduce the calculated intersection point. Thus a scale parallel to the diagonal and affixed to the localizer can be very useful. Similar scales could be placed on the two diagonals 13a and 13b of FIG. 3 in a device where two N-type structures are used.

Figure 12:
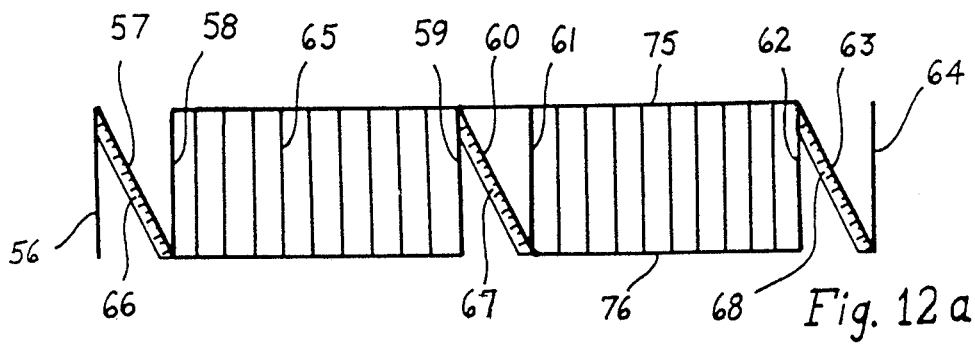
FIG. 12 shows a localizer ladder with three N-type structures fo complete CT plane determination and repeat plane localizing.
Figure 12:
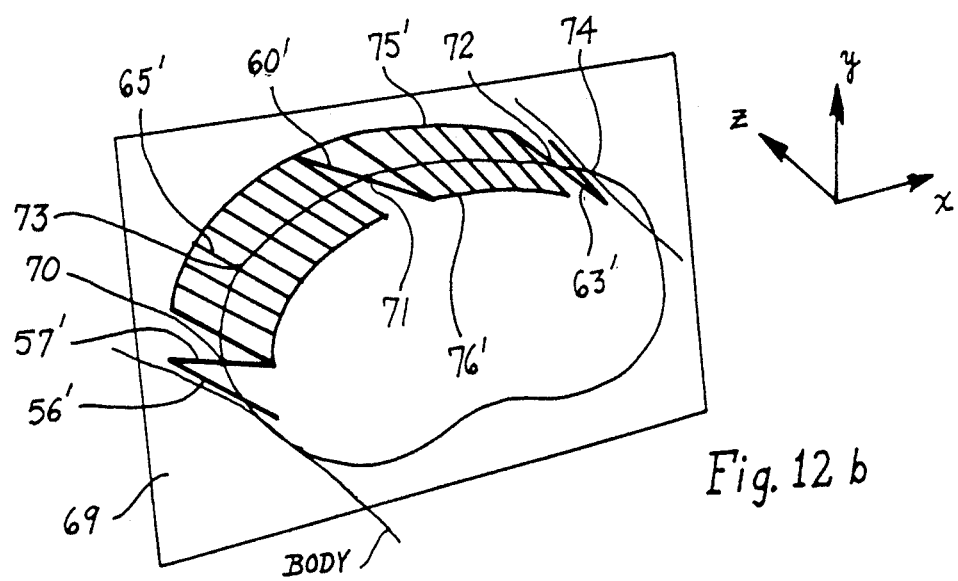

FIGS. 12a and 12b illustrate yet another N-structure plane ladder rod localizer which can be used to completely define the CT plane thus requiring no knowledge of localizer positioning or CT machine plane orientation. This involves three N-structures, the CT intersection of each determines a unique point on each of their diagonals, so that three points in the CT plane are determined which entirely determine the CT plane. This is analogous to R. Brown,'s localizer except the one of FIG. 12 is flexible to be stuck or fixed close to the skin, it also has the intermediate rods to locate skin points and there are scales near the diagonals of the N's to easily locate the calculated diagonal intersection. In FIG. 12a elements 56, 57, 58; 59, 60, 61; and 62, 63, 64 make the three N-structures. Typical rod is 65, and scales 66, 67, and 68 give proportions or distances along 57, 60, and 63. FIG. 12b shows how it might lie close to the body's skin, and CT plane 69 intersects the corresponding diagonals 57', 60', and 63' at points 70, 71, 72 which are then determined by the proportional method of R. Brown as described above for FIGS. 3, 9, 10. Points 70, 71, 72 determine plane 69 completely, and thus a planar light beam, for example, going through 70, 71, 72 would lie in the CT plane 69, and its intersection with rod 65' at point 73 would correspond to the image point 73 seen on the CT plane image. Thus 73 might be chosen as an entry point for a probe puncture. Again, a planar light beam, or some other way to mechanically or optically define a plane that could be visualized by the operator, could be used to draw the perimeter intersection 74 of plane 69 with the skin. Planar light beams or sheets or laser dispersion are standard and found on most CT scanner machines. The localizer of FIG. 12a is shown lying flat on the plane of the paper, but it could have flexible connective members 75 and 76 so that it can be conformed to the patient's body as shown in FIG. 12b by the curve members 75, 76'. Also 75, 76 could have sticky undersides to adhere to the skin. A CT scan would determine 70, 71, 72 and thus the CT plane 69 as the patient lies on the CT scanner table. This could be used immediately while the patient is still on the table for skin point localization, or the patient may be moved from the CT scanner to some remote table, and, by lining up a device on the points 70, 71, 72, the CT plane could be once again re-established. Then a stereotaxic instrument could be aligned to the 70, 71, 72 plane and the entry point 73, for example near one of the rods 65', could be used to pass a probe in an internal target which was calculated from the CT image plane. The scales 66, 67, 68 are placed near the diagonals for immediate indexing of the points 70, 71, 72. Thus the localizer of FIG. 12 can be used for repeat localizations at a location remote from the scanner table.

It is evident from the description of our invention above that it has the advantage of continuous interpolation along the axial direction. That is, because we have a diagonal element in many of the embodiments, we are able to determine in a continuous fashion the z position along one or all of the rods and along the diagonal. The only limitation in the resolution would be the degree to which the CT scanner image can resolve the centroids of the rod and diagonal image points. It is also obvious from our description that because in many of our designs the rod elements are approximately of equal length, and their ends can be approximately aligned with the axial plane, that in any approximately axial scan, all of the rod image points and the diagonal point, for that matter, will be visible in the scan. This means that one can run the entire range of the length of the localizer, that is, all of the rod intersection points, as a choice of entry point for one surgical procedure. In fact, simple linear interpolation between rods would enable a continuum of points to be determined between the rod elements themselves thus giving a full two-dimensional matrix of localization points possible with our localizer design. This continuum of interpolation points is along the curvilinear line which includes the rod image points, and a continuum of points in the axial direction achieved by variation of the z position of the scan plane itself.

Having described in detail various embodiments of our invention, it will now become apparent to those skilled in the art that many modifications can be made therein without departing from the scope of the invention as defined in the following claims. In particular, other more elaborate ladder structures or rod structures can be devised with other elaborated means to determine the z position. Overlaying rod structures with rods which are not parallel or approximately orthogonal to each other could be devised so as to essentially give a two- or three-dimensional character to the localizer and uniquely determine coordinate points or perhaps several coordinate points simulatneously,

What we claim and desire to secure by Lettters Patent of the United States are:

1. A localizer for use with CT scanning comprising at least one N-type structure, said structure comprising a planar arrangement of two parallel rods and one diagonal element running non-parallel to said rods, so that a CT scan cutting said rods and said diagonal element will enable the point of CT plane intersection with the diagonal element to be determined from the positions of the image points of said rods and said diagonal element on the CT image of the CT scan plane and rom the known positions of said rods and said diagonal element in said N-type structure, and a plurality of additional rods running substantially parallel to the two parallel rods of said N-type structure when said localizer is laid flat down on a surface, said localizer being so adapted that it can be conformed closely to the skin of a patient during CT scanning so that when said localizer is laid close to the patient's skin said rods and said diagonal element will be cut my bhe CT plane and then from the said determined intersection of said CT plane with said diagonal element and from the knowledge of the orientation of said CT plane to said localizer on the skin, one can determine the intersection point of said CT plane with any of said additional rods which in turn can be used as an entry point near the skin for passage of a probe into the patient's body.

2. The skin localizer of claim 1 and further including a scale which lies close to and parallel to said diagonal element, said scale being calibrated so that said distance between said diagonal element and the two diagonal parallel rod intersection image points are mapped into the divisions of said scale which in turn locate said intersection of said CT plane with said diagonal element.

3. The skin localizer of claim 1 in which said two parallel rods, diagonal element and additional rods comprise radioopaque material that shows up well on x-ray CT scan images.

4. The skin localizer of claim 1 in which said two parallel rods of the N-type structure and the additional rods are of substantially equal length and connected by a least one deformable connective member in such a way that one end of each of said additional rods can be aligned with said CT scan plane at the time said localizer is positioned on the patient's body and axes of the additional rods can be oriented non-parallel to said CT scan plane and said additional rods can be placed near the patient's skin and wherein said diagonal element is connected to said two parallel rods of the N-type structure such that the axis of the diagonal element remains at a fixed angular orientation to the axes of said two parallel rods whereby the distance between said intersection of said CT plane with said diagonal element and at least one of said two parallel rods as determined by their images determines the position of intersection of said scan plane with said diagonal element.

5. The skin localizer of claim 1 in which said two parallel rods, one diagonal element and additional rods are so constructed to be adapatable and visible in x-ray computerized tomographic imaging.

6. The skin localizer of claim 1 in which said two parallel rods, one diagonal element and additional rods are so constructed to be adaptable and visible in magnetic resonance imaging computerzied tomographic imaging.

7. The skin localizer of claim 1 wherein at least some of said additional rods are located between said two parallel rods.

8. A skin localizer for use with CT scanning comprising at least one triangular structure said structure comprising a planar arrangement of a first rod and one diagonal element running non parallel to said first rod, so that a CT scann cutting said first rod and diagonal element will enable the point of CT plane intersection with said first rod to be determined from the known positions of said first rod and diagonal element within said triangular structure and from knowledge of the orientation of said triangular structure with respect to the CT scanning plane, and a plurality of additional rods running substantially parallel to said first rod when said localizer is laid flat down on a surface, said localizer being so adapted that it can be conformed closely to the skin of a patient during CT scanning, and whereby when said localizer is laid close to the patient's skin so that said first rod, said diagonal element, and said additional rods are cut by the CT plane, then from the said determined intersection of said CT plane with said first rod and from the knowledge of the orientation of said CT plane to said localizer on the skin, one can determine the intersection point of said CT plane with any of said additional rods which in turn can be used as an entry point near the skin for passage of a probe into the patient's body.

9. The skin localizer of claim 8 and further including a scale which lies close to and parallel to said first rod, said scale being calibrated so that said distance between said diagonal element and first rod intersections with said CT plane as determined from the CT image is mapped into the divisions of said scale which in turn locate said intersection of said CT plane with said frist rod which lies close to said scale.

10. The skin localizer of claim 8 wherein said two parallel rods and said additional rods are of substantially equal length and connected by at least one deformable connective member in such a way that one end of each of said additional rods can be aligned with said CT scan plane at the time said skin localizer is positioned on the patient's body and the axis of the first parallel rod can be oriented non-parallel to said CT scan plane and said additional rods can be placed near the patient's skin and wherein said diagonal element is connected to said first rod so that the axis of the diagonal element remains at a fixed angular orientation to the axis of said first rod, whereby the distance between said intersection of said CT plane with said diagonal element and said first rod as determined by the images thereof on said CT scan image determines the position of intersection of said scan plane with said first rod.

11. The skin localizer of claim 8 in which said first rod, one diagonal element and additional rods are so constructed to be adaptable and visible in x-ray computerized tomographic imaging.

12. The skin localizer of claim 8 in which said first rod, one diagonal element and additional rods are so constructed to be adaptable and visible in magnetic resonance imaging computerzied tomographic imaging.

13. A skin localizing device comprising a multiplicity of at least three substantially parallel elongated rod elements and a diagonal element that is non parallel to said rod elements and is so positioned relative to said rod elements that said diagonal element comes in close proximity to each of said rods, said skin localizing device being so constructed that it can be laid on and conform to the patient's skin so that said rod elements will lie in close proximity to the patient's skin, whereby when a CT scan cuts said rod and diagonal elements, then the image of said diagonal element on said CT scan image will be in proximity to the image of a particular rod element among said rod elements so that the physical point of intersection of said CT scan plane with said diagonal element can be determined by the physical intersection of said particular rod element with said diagonal element and where by knowing the orientation of said CT scan plane relative to the patient's body, one can determine the intersection of said CT scan plane with any of the other rod elements which thereby provide a multiplicity of points in proximity to the patient's skin that can be used as entry points for passage of a probe into the patient's body.

14. A skin localizer for use with CT scanning comprising at least one triangular structure said structure comprising a planar arrangement of a first side element and a second side element running non parallel to said first side element so that a CT scan cutting said first side element and said second side element will enable the position of CT plane intersection with said triangular structure to be determined from the known positions of said first side element and side second side element within said triangular structure and from knowledge of the orientation of said triangular structure with respect to the CT scanning plane, and a plurality of additional side elements running substantiallly parallel to each other when said localizer is laid flat down on a surface, said localizer being so adapted that it can be conformed closely to the skin of a patient during CT scanning, and whereby when said localizer is laid close to the patient's skin so that said first side element, said second element and said additional side elements are cut by the CT plane, then from the said determined intersection of said CT plane with said triangular structure and from the knowledge of the orientation of said CT plane to said localizer on the skin, one can determine the intersection point of said CT plane with any of said additional side elements which in turn can be used as an entry point near the skin for passage of a probe into the patient's body.

15. The skin localizer of claim 14 and further including a scale which is attached to said triangular structure, said scale being calibrated so that said distance between said first side element and said second side element intersections with said CT plane as determined from the CT image is mapped into the divisions of said scale which in turn locate said intersection of said CT plane with said triangular structure in proximity to said scale.

16. The skin localizer of claim 14 wherein said additional rods are of substantially equal length and connected by at least one deformable connective member in such a way that one end of each of said additional rods can be aligned with said CT scan plane at the time said skin localizer is positioned on the patient's body and said additional rods can be placed near the patient's skin and wherein said first side element is connected to second side element so that the axis of said first side element remains at a fixed angular orientation to the axis of said second side element whereby the distance between said intersection of said CT plane with said first side element and said second side element as determined by the images thereof on said CT scan image determines the position of intersection of said scan plane with said first and said second side elements and with said additional rods.

17. The skin localizer of claim 14 in which said first and second side elements and the additional side elements are so constructed to be adaptable and visible in X-ray computerized tomographic imaging.

18. The skin localizer of claim 14 in which said first and second side elements and the additional side elements are so constructed to be adaptable and visible in magnetic resonance imaging computerized tomographic imaging.

* * * * *